(12) United States Patent
Jaeger et al.

(10) Patent No.: US 9,943,434 B2
(45) Date of Patent: Apr. 17, 2018

(54) VISCOELASTIC ELEMENT

(71) Applicant: Bauerfeind AG, Zeulenroda-Triebes (DE)

(72) Inventors: Thorsten Jaeger, Plauen (DE); Dominique Panzer, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 0 days.

(21) Appl. No.: 14/700,646

(22) Filed: Apr. 30, 2015

(65) Prior Publication Data

US 2015/0230968 A1   Aug. 20, 2015

Related U.S. Application Data

(63) Continuation of application No. PCT/EP2013/070557, filed on Oct. 2, 2013.

(30) Foreign Application Priority Data

Oct. 30, 2012   (DE) .................. 10 2012 021 696

(51) Int. Cl.
*A61F 5/30* (2006.01)
*B32B 3/26* (2006.01)
(Continued)

(52) U.S. Cl.
CPC .............. *A61F 5/30* (2013.01); *A43B 13/386* (2013.01); *A61F 5/0123* (2013.01); *B32B 3/263* (2013.01);
(Continued)

(58) Field of Classification Search
CPC ........ A43B 13/386; A61F 5/30; A61F 5/0123; A61F 5/34; B32B 3/263; B32B 2307/536; B32B 2535/00; B32B 3/28; B32B 3/30
(Continued)

(56) References Cited

U.S. PATENT DOCUMENTS 4,896,441 A * 1/1990 Galasso ............... A43B 7/1415
  36/140
5,203,793 A * 4/1993 Lyden .................. A43B 3/0063
  12/142 N
(Continued)

FOREIGN PATENT DOCUMENTS

CN   201813948       5/2011
CN   201813948 U *   5/2011   ............. A43B 13/04
(Continued)

OTHER PUBLICATIONS

English language International Preliminary Report on Patentability and Written Opinion for International Patent Application No. PCT/EP2013/070557.
(Continued)

*Primary Examiner* — Maria V Ewald
*Assistant Examiner* — Ethan Weydemeyer
(74) *Attorney, Agent, or Firm* — Edell, Shapiro & Finnan LLC

(57) ABSTRACT

Elements for at least partially viscoelastic medical products, or for at least partially viscoelastic orthopedic aids, and for at least partially viscoelastic medical products are provided. In addition, at least partially viscoelastic orthopedic aids are provided that contain such elements, or that consist of such elements and the use of such elements.

9 Claims, 3 Drawing Sheets

(51) Int. Cl.
A43B 13/38 (2006.01)
A43B 13/40 (2006.01)
A61F 5/01 (2006.01)

(52) U.S. Cl.
CPC ..... *B32B 2307/536* (2013.01); *B32B 2535/00* (2013.01); *Y10T 428/24521* (2015.01)

(58) Field of Classification Search
USPC ................... 36/71, 43–44, 140–182; 602/26
See application file for complete search history.

(56) References Cited

U.S. PATENT DOCUMENTS

| 7,506,459 | B2* | 3/2009 | Grisoni | A43B 7/1425 36/180 |
|---|---|---|---|---|
| 2001/0045028 | A1 | 11/2001 | Crane et al. | |
| 2004/0261294 | A1* | 12/2004 | Kawata | A43B 1/0027 36/44 |
| 2005/0039349 | A1 | 2/2005 | Grisoni et al. | |
| 2006/0230643 | A1 | 10/2006 | Affleck | |
| 2011/0087145 | A1 | 4/2011 | Farrow et al. | |
| 2011/0247235 | A1* | 10/2011 | de Roode | A43B 7/142 36/44 |
| 2012/0090198 | A1* | 4/2012 | Stratten | A43B 1/0045 36/44 |

FOREIGN PATENT DOCUMENTS

DE 202007009220 8/2007
WO 2007149429 12/2007

OTHER PUBLICATIONS

International Search Report in corresponding International Application No. PCT/EP2013/07557, dated Dec. 2013. 2013.

* cited by examiner

VISCOELASTIC ELEMENT

CROSS REFERENCE TO RELATED APPLICATIONS

This application is a continuation of International Application No. PCT/EP2013/070557, filed on Oct. 2, 2013, which claims priority under 35 U.S.C. § 119 to Application No. DE 102012021696.3 filed on Oct. 30, 2012, the entire contents of which are hereby incorporated by reference.

FIELD OF THE INVENTION

The invention relates to elements for at least partially viscoelastic medical products or at least partially viscoelastic orthopedic aids, at least partially viscoelastic medical products or at least partially viscoelastic orthopedic aids containing or consisting of such elements, and to the use of such elements.

BACKGROUND

Heel cushions are viscoelastic orthopedic aids. They are often made of a single material, i.e. a single component, or may have a further, softer material integrated in a defined region in this component, so that, for example, a heel spur may be relieved. In this way, however, indication-based relief is possible only to a limited extent.

Other viscoelastic orthopedic aids and viscoelastic medical products such as pads are also usually made of a single material.

An object of the invention is to provide novel elements for viscoelastic medical products, or partially viscoelastic orthopedic aids, which are improved over the prior art. In particular, the elements should provide improved indication-based support, relief, stimulation, movement control and/or proprioception of the adjacent body region, for example, the sole of the foot, the heel, or the knee.

SUMMARY

The technical problem underlying the object of the invention is solved by providing a viscoelastic element, in particular, by providing an element for an at least partially viscoelastic medical product, or for an at least partially viscoelastic orthopedic aid, whereby the element includes at least a first layered component and a second layered component, the first component is harder than the second component, a surface of the first component is connected to a surface of the second component, the element has at least two zones of a different hardness or viscoelasticity on its surface, and the area of the first component connected to the second component has a plurality of protrusions. The hardness or viscoelasticity of these zones is determined by the height, width, and/or distribution of the protrusions in a zone of the element.

It has surprisingly been found that, due to the inventive layered design of at least one first and one second component of a different hardness and due to the configuration of the surface of the first component, which is connected to the second component, the viscoelasticity of an element can be set with a plurality of protrusions. In particular, it has been found that zones of a different hardness or viscosity can advantageously be produced in the element by the inventive layered design and by the height, the number, and the specific shape of the protrusions.

Thus, zones of different viscoelasticity can be produced in an indication-based manner and an exact position, where the viscoelasticity of a zone with respect to the material used can be freely chosen, and the element can have more than two different viscoelasticities even if only two components are used, with no further components.

The protrusions, for example, pegs and/or waves, may advantageously act in as stimulation points which specifically stimulate the adjacent body surface by means of pressure.

In addition, the interface between the first component and the second component is increased by the protrusions, so that the two components can be, or are, better connected to one another. In addition, a softer material need not necessarily be integrated into a base material, but rather a simple layered combination of materials may be used.

Since the two layered components are connected to one another in each case via one of their surfaces and the first component has protrusions on this surface, it is provided that the surface of the second component at this position have a corresponding recess, so that the two components are connected to each other by a lock and key principle at their corresponding surfaces, or that the surface of the second component is a negative of the surface of the first component.

The surfaces of the first and second components, which are not connected to the respective other component, can have any desired shape, for example, they may be smooth.

In a preferred embodiment, the first and the second component have a different Shore hardness.

In a preferred embodiment, the first and the second component are made of materials with a different Shore hardness. In a preferred embodiment, the first and second components are made of different materials with a different Shore hardness.

The Shore hardness of a component can be determined by the choice of the respective materials and/or by the structure of the material. Without being tied to the theory, for example, the first and the second component can consist of the same material, a substantially identical material, or a similar material, wherein nevertheless due to the respective structural properties of the material, they have a different Shore hardness.

In a preferred embodiment, the first and the second component consist of viscoelastic materials.

A person skilled in the art is familiar with suitable materials, in particular viscoelastic materials. He can also readily determine the Shore hardness of the materials. The suitable materials are preferably viscoelastic.

The suitable materials include, for example, those used in viscoelastic medical products or in viscoelastic orthopedic aids from the prior art, for example in pads, insoles, or heel cushions.

Thermoplastic and duroplastic elastomers, for example, are suitable materials.

The protrusions may have any desired shape.

In a preferred embodiment, the elevations are peg-shaped or wave-shaped.

In a preferred embodiment, the elevations are peg-shaped. In a preferred embodiment the first component comprises a plurality of pegs as elevations.

In the context of the present invention, a peg is understood to mean a protruding piece for connecting the two components. A peg is preferably configured such that the length and width of the peg are similar, and that in particular the peg is at most 5 times longer in cross-section than it is wide. A peg can have any suitable shape, for example the shape of a cube, a parallelepiped, a pyramid, a cone, a sphere, or a cylinder. The cross-section of a peg can have any two-dimensional shape, for example, a round, oval, elliptical or polygonal shape, for example, be quadrangular, in particular square, pentagonal, hexagonal, octagonal or star-shaped. The cross-section of a peg can be the same throughout or change along the length of the peg, in particular taper when viewed from the base surface.

Of course, the first component may also comprise pegs of different shapes, as the viscoelasticity can also be influenced by the shape of the pegs.

Of course, pegs and waves may be combined as protrusions.

The viscoelasticity of a zone is preferably determined by the height of the local protrusions of the first, harder component, that is, by the length of the protrusions as viewed from the base. The higher the protrusions, the harder the corresponding zone.

Alternatively, the viscoelasticity of a zone is determined by the distribution of the local protrusions of the first, harder component. The more protrusions per unit area, the harder the appropriate zone.

Of course, a combination of the height and distribution of the protrusions is advantageously possible to set the desired viscoelasticity in a zone.

In a preferred embodiment, the first component and/or the second component is made of a transparent or translucent material. In this way, the inventive structure of the element is visible, and a person skilled in the art can see the exact position of the zones of different viscoelasticity.

In a preferred embodiment, the element consists of two layered components.

In an alternative embodiment, the element has at least a third component.

The third component can likewise be layered, and can form another layer of the element as a further layer on the first component or on the second component. The same applies to a fourth component and to more components.

In a preferred embodiment, the third component is a layer covering the first component or the second component. In a preferred embodiment, the third component is a film, a fabric, or a nonwoven fabric. In a particularly preferred embodiment, the third component is a foil lamination.

In a preferred embodiment, the third component is a layer covering the first component, and the fourth component is a layer covering the second component. In a preferred embodiment, the third and the fourth components are a foil, a fabric, or a nonwoven fabric. In a particularly preferred embodiment, the third and the fourth components are a foil lamination.

A third layered component can in particular serve to form a comfortable, for example, non-sticky or cool contact surface of the element with the corresponding body part of the patient, for example, the sole of the foot.

In a partial region of the first component and/or of the second component, the third component can, however, also extend over the layer formed by the first component and/or the second component, or be embedded in the layer formed by the first component and/or the second component. The same applies to a fourth component and more components.

In a preferred embodiment, the element, for example in the form of a pad, an insole, or a heel cushion, can be available in a finished condition. Alternatively, however, it can also be provided that the element is reworked, so that for example an orthopedic shoe technician can still individually adjust the shape of an inventive element, such as a shoe insole according to the invention or an inventive heel cushion.

In a preferred embodiment the element is an element for an orthopedic medical product, that is, in particular, a component of an orthopedic medical product. In an alternative embodiment, the element is an orthopedic medical product.

In a preferred embodiment, the element is part of an insole or of a heel cushion.

In a preferred embodiment, the element is an insole or heel cushion.

In a preferred embodiment, it is a viscoelastic insole or a viscoelastic heel cushion.

In a preferred embodiment, the first component forms the lower portion of the insole or of the heel cushion, and the second component constitutes the upper part of the insole or of the heel cushion. In an alternative embodiment, the first component forms the upper part of the insole or of the heel cushion and the second component forms the lower part of the insole or of the heel cushion.

In a preferred embodiment, the element is a component of a pad. In a preferred embodiment the element is a pad, preferably a viscoelastic pad, in particular, an annular or wave-shaped pad.

Knee joint ortheses with a ring-like or half-ring-like pad enclosing the patella of the knee joint in an applied state of the orthesis are known. Such orthotics are known to be configured as a stocking or tubular elastic knitted fabric. A pad is inserted into the knitted fabric in the region of the patella. The pad supports the patella and fixes the latter in the joint in a physiologically correct position, especially in connection with the pressure applied by the elastic knitted fabric. Known pads are made of an elastic material such as silicone rubber or polyurethane or similar materials.

The pad is in particular ring-shaped in its basic form (pad base) and encloses the patella. In another particular embodiment, the pad is horseshoe-shaped, that is, it is configured in a half-ring design and encloses the patella at least distally.

The novel pad is used in a manner known per se, preferably in an elastic knitted orthesis. The pad is pressed against the knee joint in the region of the patella via the knitted orthesis. The distal protrusions exert their effect especially in conjunction with the elastic base fabric of the bandage and interact with the latter by way of the movements.

As a result of the construction according to the invention, the pad can advantageously have zones of a different hardness, so that they press against the knee joint in the region of the patella with different intensities.

The subject matter of the invention also is a medical product, in particular an orthopedic medical product or orthopedic aid, comprising an inventive element. The subject matter of the invention also is a medical product, in particular an orthopedic medical product or orthopedic aid, consisting of an element according to the invention.

The medical product or orthopedic aid preferably is an insole, a heel cushion, or a pad.

The subject matter of the invention also are insoles and heel cushions containing elements according to the invention.

The subject matter of the invention also is the therapeutic and/or prophylactic use of insoles and heel cushions containing elements of the invention, for physiological cushioning and support in the heel, midfoot, and forefoot region, in particular for the treatment of heel spurs, arthrosis of the leg joints, achillodynia, Haglund's deformity, leg length difference, and hind foot complaints.

The subject matter of the invention also is a knee joint orthesis or bandage containing the pad according to the invention. This is designed especially as a knitted orthesis with an inserted inventive pad.

The subject matter of the invention also is the use of the pad according to the invention with the protrusions formed thereon to improve and/or to secure the positioning of the joint orthesis on the body joint.

The subject matter of the invention also is the therapeutic and/or prophylactic use of the pad according to the invention in a knee joint orthesis to support the congruent closure between the infrapatellar joint elements. The prophylactic and/or therapeutic use of the pad according to the invention in a knee joint orthesis to support the biomechanical function of the infrapatellar fat pad of the knee joint, in particular its joint-supporting function is also the subject matter of the invention.

The subject matter of the invention also is the prophylactic and/or therapeutic use of the pad according to the invention in a knee joint orthesis to stabilize the patella of the knee joint in the extended position.

The subject matter of the invention also is the prophylactic and/or therapeutic use of the pad according to the invention in a knee joint orthesis for the treatment of anterior knee syndrome.

The subject matter of the invention also is the prophylactic and/or therapeutic use of the pad according to the invention in a knee joint orthesis for the treatment of edemas in the infrapatellar fat pads of the knee joint.

The subject matter of the invention also is a process for producing an element according to the invention in which two materials of a different Shore hardness are sequentially injected or poured into a tool. A person skilled in the art is familiar with the appropriate tools and process parameters in the casting and injection molding technology.

The subject matter of the present invention also is the use of two materials of a different Shore hardness for the manufacture of an orthopedic medical product according to the invention or of an orthopedic aid according to the invention for the treatment of the above-mentioned clinical conditions.

BRIEF DESCRIPTION OF THE DRAWINGS

Example embodiments will now be described with reference to the drawings.

DETAILED DESCRIPTION

Figure 1:
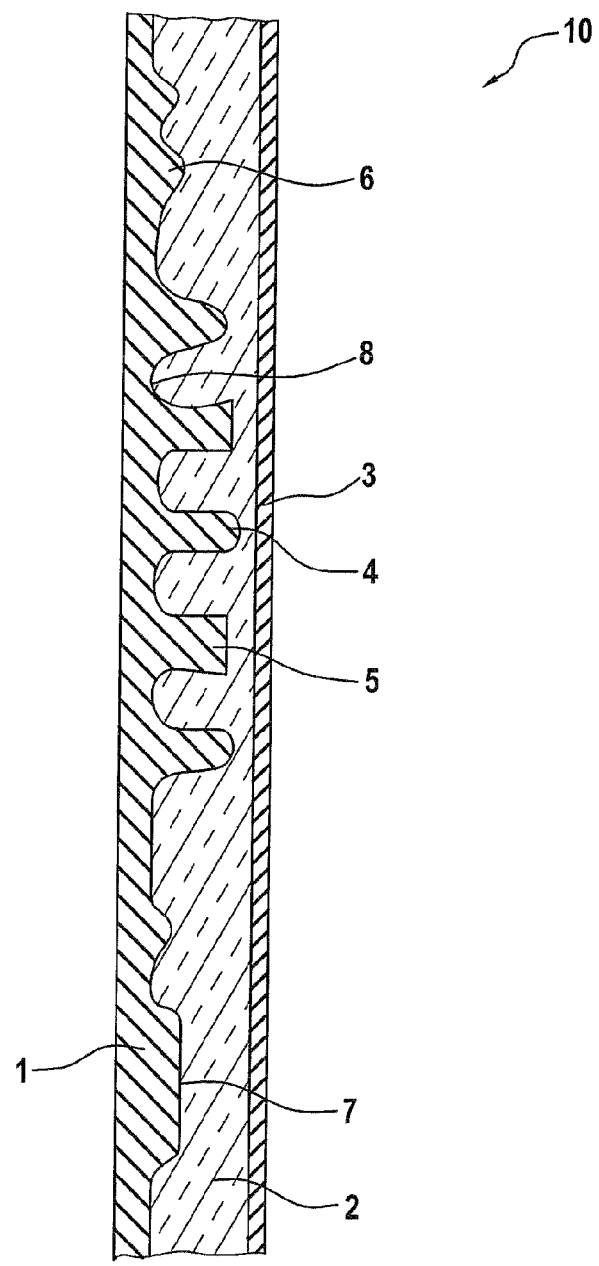
FIG. 1 shows a cross-sectional detail of an element according to an example embodiment.

FIG. 1 shows a cross-sectional detail of an element 10 according to an example embodiment. The element 10 according to the example embodiment is composed of a first layered component 1 and a second layered component 2. The first component 1 and the second component 2 each consist of a viscoelastic material. The first component 1 is made of a viscoelastic material that is harder than the second component 2. In addition, an optional third layered component 3 is applied to the second layered component 2.

The surface of the first component 1 connected to the second component 2 has different protrusions 4, 5, 6, 7. In a region of the detail, the protrusions 4, 5 are comparatively high. Due to the high protrusions 4, 5 of the first component 1, this zone comparatively contains more of the harder material of the first component 1. As a result, this zone of the element 10 is harder, or has a lower viscoelasticity, than a zone in which there are no, or only comparatively low, protrusions 6, 7.

The protrusions can have different shapes. Peg-like protrusions 4, 5, 6 can, for example, be provided, wherein the shape of the pegs can vary; for example pegs 4 that are round in cross-section or square in cross-section 5 can be provided. Alternatively, wave-like protrusions 7 can be added to the pegs.

The hardness or viscoelasticity of a specific zone of the element 10 can be determined not only by the height of the protrusions 4, 5, 6, 7, but also by the shape and number of the protrusions. Thus, due to the wave-like protrusions 7 in the zone, more and harder material of the first component 1 is available there than in the zone of the peg-like protrusions 6, so that the zone around the protrusions 7 is harder or less viscoelastic than the zone around the protrusions 6.

The surface of the second component 2, which is connected to the first component 1, provides a negative of the surface of the first component 1, which is connected to the second component 2. Thus, the second component 2 has protrusions 8 at points where the first component 1 has none.

The plurality of protrusions 4, 5, 6, 7 results in a significant enlargement of the interface between the first component 1 and the second component 2. In addition, the interface is not flat. This results in an improved connection of the first component 1 to the second component 2.

An optional third component 3 can, for example, be applied to the surface of the element in contact with the body of the patient. It can, for example, consist of fabric and thus contribute to a better wearing comfort.

Figure 2:
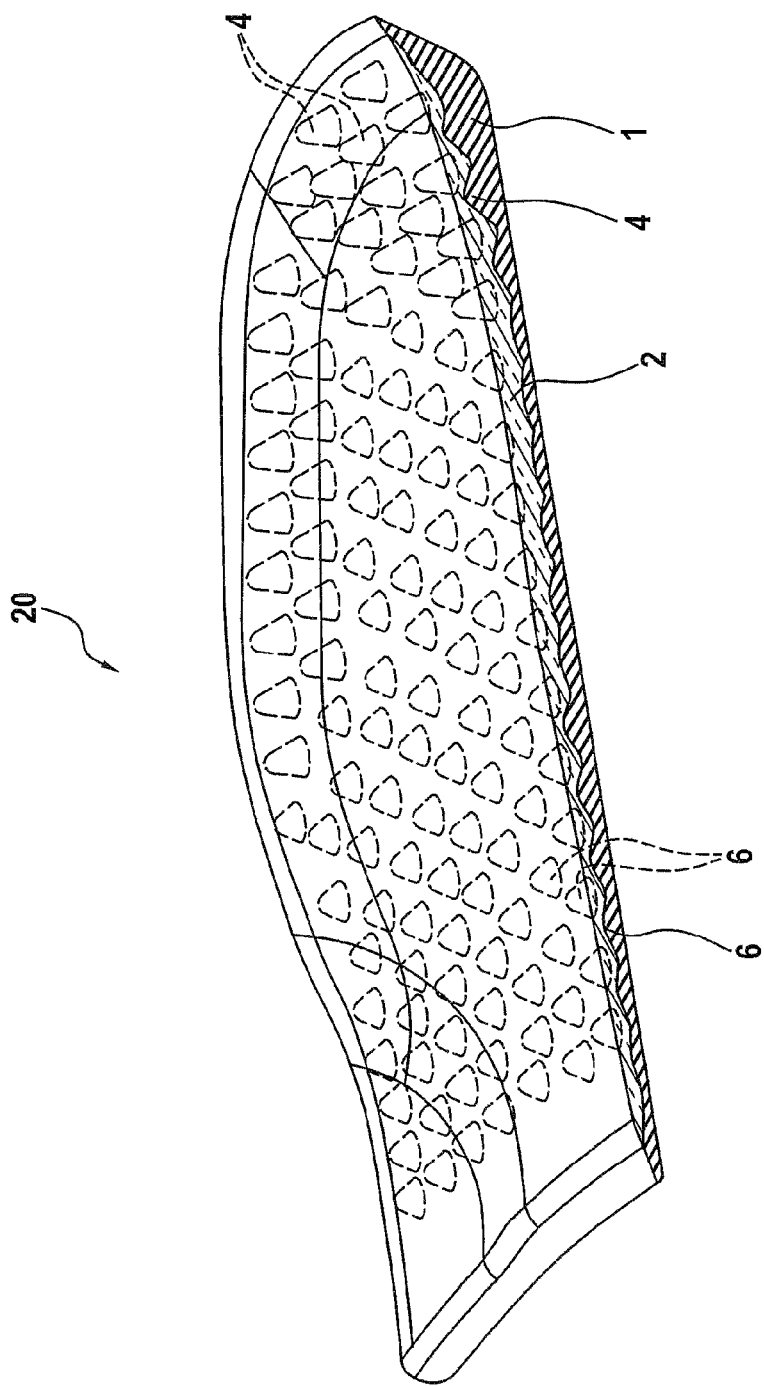
FIG. 2 shows a cross-section and a partial top view of an insole according to an example embodiment.

FIG. 2 shows a cross-section and a partial view of an insole 20 according to another example embodiment. The insole is made of a harder, less viscoelastic first component 1 and a softer more viscoelastic second component 2. The basic structure of the example embodiment, and the resulting advantages and possible modifications are based on the elements of the example embodiment of FIG. 1.

The harder first component 1 is arranged below, that is, in the direction of the shoe, and the softer second component 2 is arranged above, that is, in the direction of the foot. As a support surface for the foot, the softer second component 2 contributes to the wearing comfort. If necessary, this arrangement can, however, also be reversed.

The second component 2 consists of a translucent or transparent material. Therefore, the overall construction of the insole 20 and in particular the interface between the first component 1 and second component 2 is visible.

The first component 1 has a plurality of protrusions 4, 6. In this case, surface zones are provided, which have a high density of high peg-like protrusions 4 and thus are harder, less viscoelastic, and thus more stable, and surface zones are provided that have a lower density of low peg-like protrusions 6, and thus are softer and more viscoelastic. The harder zones with the higher protrusions 4 are used, for example, to support the foot, while the areas with low protrusions 6 constitute relieving regions of the insole. In addition, higher protrusions can also be provided as proprioception points.

Figure 3:
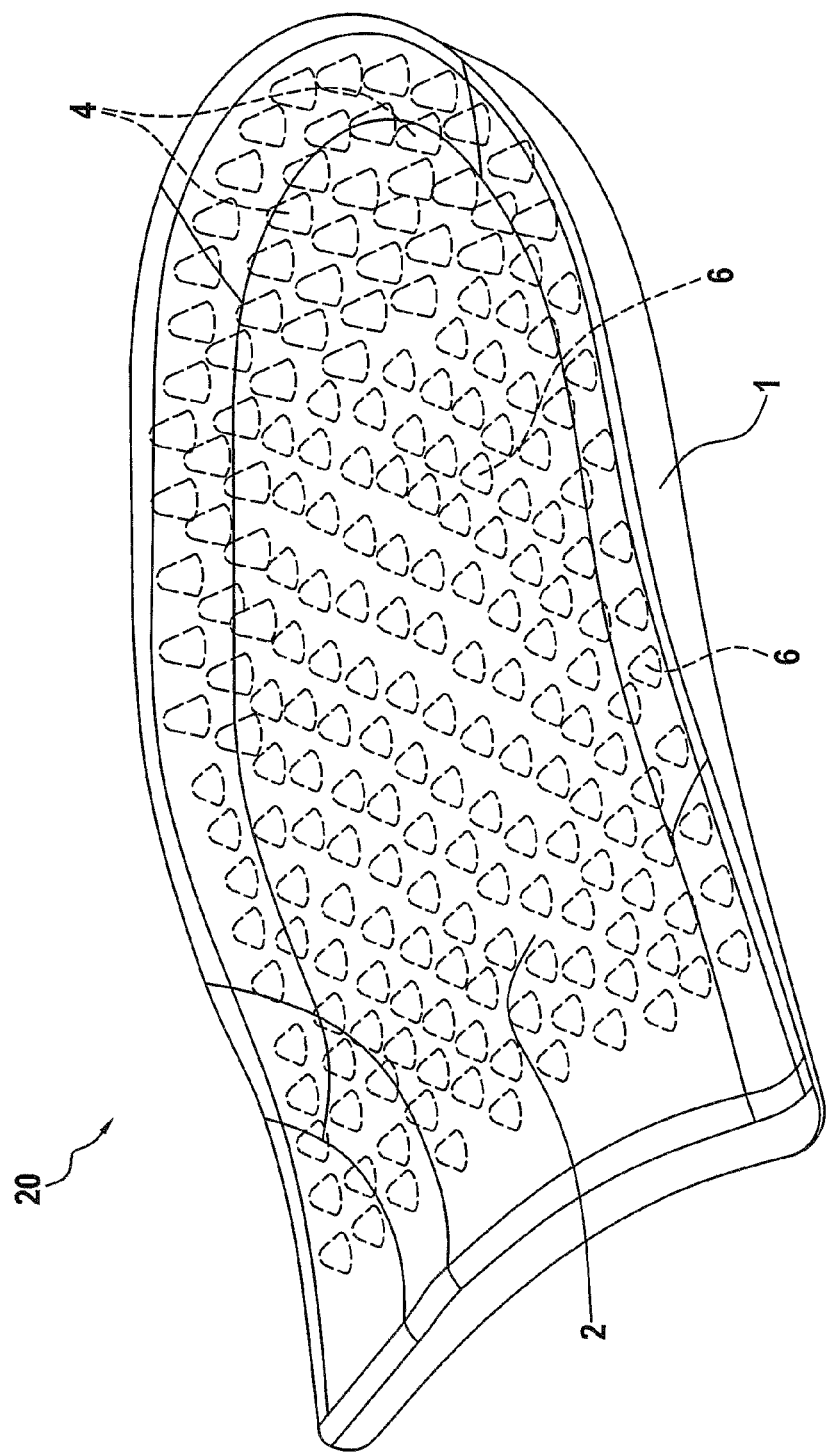
FIG. 3 shows a full view of the insole according to the example embodiment shown in FIG. 2.

FIG. 3 shows the full view of the insole 20 according to an example embodiment shown in FIG. 2. This again consists of a harder, less viscoelastic first component 1, a softer, more viscoelastic second component 2, wherein the first component has a plurality of peg-like protrusions 4, 6.

In summary, an element 10 is provided for an at least partially viscoelastic orthopedic medical product, or for an at least partially viscoelastic orthopedic aid, wherein the element 10 comprises at least a first layered component 1 and a second layered component 2, wherein the first component 1 is harder than the second component 2, wherein a surface of the first component 1 is connected to a surface of the second component 2, and wherein said element 10 has at least two zones of different hardness on its surface. Element 10 is characterized in that the surface of the first component 1 connected to the second component 2 has a plurality of protrusions 4, 5, 6, 7, wherein the hardness of these zones is determined by the height, width, and/or distribution of the protrusions 4, 5, 6, 7 in a zone of the element 10.

According to an example embodiment, element 10 is an insole 20 or a heel cushion.

According to a further example embodiment, the first component 1 forms the upper or lower portion of the insole 20 or of the heel cushion, and the second component 2 accordingly forms the lower or upper part of the insole 20 or of the heel cushion.

According to another example embodiment, element 10 is a pad.

According to a further example embodiment, the first 1 and the second 2 components consist of materials of different Shore hardness.

The protrusions 4, 5, 6, 7 are peg-like or wave-like.

The first component 1 has a plurality of pegs as protrusions 4, 5, 6, 7.

The pegs have a round 4, oval, ellipsoidal, or polygonal 5 cross-section.

The first component 1, and/or the second component 2 consist of a transparent or translucent material.

According to another example embodiment, element 10 also comprises at least a third component 3. The third component 3 is likewise layered and forms a further layer on the first component 1, or on the second 2 component. In a partial region of the first component 1, and/or of the second component 2, the third component 3 extends over the layer formed by the first component 1 and/or the second component 2, or is embedded in the layer formed by the first component 1 and/or the second component 2.

According to an example embodiment, an orthopedic medical product or orthopedic aid is provided comprising an element 10 as described above.

According to a further example embodiment, the orthopedic medical product or orthopedic aid is an insole 20, a heel cushion, or a pad.

What is claimed is:

1. An element for an at least partially viscoelastic orthopedic medical product, or for an at least partially viscoelastic orthopedic aid, comprising: at least one first layered component; and at least one second layered component,
    wherein the at least one first layered component has a hardness that is greater than a hardness of the at least one second layered component,
    wherein each of the at least one first layered component and the at least one second layered component consist of materials of different Shore hardness,
    wherein a surface of the at least one first layered component is connected to a surface of the at least one second component utilizing a lock and key mechanism such that the surface of the at least one first component that is connected to the at least one second component comprises a plurality of protrusions that are fitted into a plurality of corresponding recesses provided in the surface of the at least one second layered component which forms a counterpart of the surface of the at least one first layered component,
    wherein the surface of the at least one first layered component and the surface of the at least one second layered component that are not connected are smooth,
    wherein the element comprises at least two zones of different hardness on a surface of the element, each of the at least two zones including a plurality of protrusions of the first component and each of the at least two zones having the different hardness on the surface of the element as a result of differences in a height, a width, and/or a distribution of the plurality of protrusions and of the plurality of corresponding recesses in each of the at least two zones of the element,
    wherein, for a region of the element having a constant thickness with regard to both the at least one first layered component and the at least one second layered component the region comprises multiple protrusions of the at least one first layered component into the at least one second layered component and contains more of the at least one first layered component than of the at least one second layered component and
    wherein the element comprises an insole or a heel cushion.

2. The element according to claim 1, wherein the at least one first layered component forms an upper or lower portion of the insole or of the heel cushion, and
    wherein the at least one second layered component forms a lower or upper part of the insole or of the heel cushion.

3. The element according to claim 2, wherein the element comprises a pad.

4. The element according to claim 2, wherein the protrusions are peg-like or wave-like protrusions.

5. The element according to claim 2, wherein the at least one first layered component comprises a plurality of pegs as protrusions.

6. The element according to claim 5, wherein the pegs have a round, an oval, an ellipsoidal, or a polygonal cross-section.

7. The element according to claim 2, wherein the element further comprises at least one third component.

8. The element according to claim 7, wherein the third component is layered like the at least one first layered component and the at least one second layered component, and
    wherein the third component forms a further layer on the at least one first layered component, or on the at least one second layered component.

9. The element according to claim 7, wherein, in a partial region of the at least one first layered component, and/or of the at least one second layered component, the third component extends over a layer formed by the at least one first layered component and/or the at least one second layered component, or is embedded in the layer formed by the at least one first layered component and/or the at least one second layered component.

* * * * *